US012721499B2

(12) United States Patent
Diolaiti et al.

(10) Patent No.: US 12,721,499 B2
(45) Date of Patent: Sep. 1, 2026

(54) SYSTEMS AND METHODS FOR SAFE OPERATION OF A DEVICE

(71) Applicant: Intuitive Surgical Operations, Inc., Sunnyvale, CA (US)

(72) Inventors: Nicola Diolaiti, Menlo Park, CA (US); David W. Bailey, Portola Valley, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 227 days.

(21) Appl. No.: 18/490,302

(22) Filed: Oct. 19, 2023

(65) Prior Publication Data

US 2024/0115112 A1 Apr. 11, 2024

Related U.S. Application Data

(63) Continuation of application No. 16/632,964, filed as application No. PCT/US2018/044419 on Jul. 30, 2018, now Pat. No. 11,826,017.

(Continued)

(51) Int. Cl.

*A61B 34/30* (2016.01)
*A61B 1/00* (2006.01)

(Continued)

(52) U.S. Cl.

CPC ...... *A61B 1/00042* (2022.02); *A61B 1/00006* (2013.01); *A61B 1/0004* (2022.02);

(Continued)

(58) Field of Classification Search

CPC .............. A61B 1/00042; A61B 1/0004; A61B 1/00006; A61B 34/20; A61B 34/35; A61B 17/00234

See application file for complete search history.

(56) References Cited

U.S. PATENT DOCUMENTS 6,380,732 B1 * 4/2002 Gilboa .................. G01S 13/874 89/41.21
6,389,187 B1 5/2002 Greenaway et al.

(Continued)

FOREIGN PATENT DOCUMENTS

CN 103315779 A 9/2013
CN 104714638 A 6/2015

(Continued)

OTHER PUBLICATIONS

Extended European Search Report for Application No. EP18842139.0 mailed on Mar. 18, 2021, 07 pages.

(Continued)

*Primary Examiner* — Vi X Nguyen

(74) *Attorney, Agent, or Firm* — Haynes and Boone, LLP.

(57) ABSTRACT

A control system for a device includes a processor configured to receive, via one or more sensors, a contact signal indicating that an operator is in contact with an input control of an input control console coupled to the control system. The processor is further configured to determine whether the contact signal is an activation signal. The processor is further configured to receive an input representing a commanded motion of the device at the input control. The processor is further configured to execute the commanded motion if the processor determines that the contact signal is the activation signal.

21 Claims, 6 Drawing Sheets

Related U.S. Application Data

(60) Provisional application No. 62/539,368, filed on Jul. 31, 2017.

(51) Int. Cl.
*A61B 17/00* (2006.01)
*A61B 34/20* (2016.01)
*A61B 34/35* (2016.01)
*A61B 90/00* (2016.01)

(52) U.S. Cl.
CPC ........ *A61B 17/00234* (2013.01); *A61B 34/20* (2016.02); *A61B 34/35* (2016.02); *A61B 90/06* (2016.02); *A61B 2017/00336* (2013.01); *A61B 2034/301* (2016.02); *A61B 2090/061* (2016.02)

(56) References Cited

U.S. PATENT DOCUMENTS

| | | | | |
|---|---|---|---|---|
| 7,316,681 | B2 | 1/2008 | Madhani et al. | |
| 7,772,541 | B2 | 8/2010 | Froggatt et al. | |
| 8,900,131 | B2 | 12/2014 | Chopra et al. | |
| 9,259,274 | B2 | 2/2016 | Prisco | |
| 9,452,276 | B2 | 9/2016 | Duindam et al. | |
| 10,512,515 | B2 | 12/2019 | Bailey | |
| 11,612,384 | B2 | 3/2023 | Duindam et al. | |
| 2006/0013523 | A1 | 1/2006 | Childlers et al. | |
| 2006/0276775 | A1 | 12/2006 | Rosenberg et al. | |
| 2010/0256558 | A1 | 10/2010 | Olson et al. | |
| 2011/0144806 | A1 * | 6/2011 | Sandhu | A61B 34/71 700/264 |
| 2013/0035697 | A1 | 2/2013 | Ogawa et al. | |
| 2015/0120043 | A1 | 4/2015 | Howard et al. | |
| 2015/0335388 | A1 | 11/2015 | Iida et al. | |
| 2017/0071687 | A1 | 3/2017 | Cohen et al. | |
| 2017/0119483 | A1 | 5/2017 | Cohen et al. | |
| 2017/0181801 | A1 | 6/2017 | Griffiths et al. | |
| 2017/0312043 | A1 | 11/2017 | Ogawa et al. | |
| 2018/0297214 | A1 | 10/2018 | Lessing et al. | |
| 2020/0155252 | A1 | 5/2020 | Diolaiti et al. | |

FOREIGN PATENT DOCUMENTS

| | | | |
|---|---|---|---|
| CN | 105101905 | A | 11/2015 |
| CN | 106413582 | A | 2/2017 |
| CN | 106716071 | A | 5/2017 |
| DE | 102014016824 | A1 | 5/2016 |
| JP | 2003344780 | A | 12/2003 |
| JP | 2005309600 | A | 11/2005 |
| JP | 2012071406 | A | 4/2012 |
| JP | 2014014424 | A | 1/2014 |
| JP | 2014124229 | A | 7/2014 |
| JP | 2015141595 | A | 8/2015 |
| WO | WO-2011028627 | A2 | 3/2011 |
| WO | WO-2011123595 | A1 | 10/2011 |
| WO | WO-2014150509 | A1 | 9/2014 |
| WO | WO-2016025440 | A1 | 2/2016 |
| WO | WO-2016025465 | A1 | 2/2016 |
| WO | WO-2016114090 | A1 | 7/2016 |
| WO | WO-2016136614 | A1 | 9/2016 |
| WO | WO-2017014301 | A1 | 1/2017 |
| WO | WO-2017020081 | A1 | 2/2017 |
| WO | WO-2018005680 | A1 | 1/2018 |
| WO | WO-2018005928 | A1 | 1/2018 |

OTHER PUBLICATIONS

International Preliminary Report on Patentability for Application No. PCT/US2018/044419, mailed on Feb. 13, 2020, 09 pages.

International Search Report and Written Opinion for Application No. PCT/US2018/044419, mailed on Nov. 27, 2018, 13 pages (ISRG10760/PCT).

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR SAFE OPERATION OF A DEVICE

CROSS-REFERENCE TO RELATED APPLICATIONS

This patent application is a continuation of U.S. patent application Ser. No. 16/632,964, filed Jan. 22, 2020, which is the U.S. National Phase of International Application No. PCT/US2018/044419, filed Jul. 30, 2018, which designated the U.S. and claims priority to and the benefit of U.S. Provisional Application 62/539,368, filed Jul. 31, 2017, all of which are incorporated by reference herein in their entirety.

FIELD

The present disclosure is directed to systems and methods for safely operating a device, such as a steerable elongate medical device, using an input control console.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. One such minimally invasive technique is to use a flexible and/or steerable elongate device, such as a catheter, that can be inserted into anatomic passageways and navigated toward a region of interest within the patient anatomy. Control of such an elongate device by medical personnel can involve the management of several degrees of freedom including at least the management of insertion and retraction of the elongate device as well as steering of the device in a teleoperated manner using a master assembly. In addition, different modes of operation may also be supported.

Operation of a medical device, such as a flexible and/or steerable elongate device within the body of a patient presents risks to the patient when using a master assembly when the master assembly is inadvertently or accidentally actuated.

Accordingly, it would be advantageous to provide systems and methods that help limit undesirable damage to subject materials, such as the tissue of a patient, when commanding motion of a device.

SUMMARY

The embodiments of the invention are best summarized by the claims that follow the description.

Consistent with some embodiments, a control system for a device includes a memory and a processor coupled to the memory. The processor may be configured to determine, using one or more sensors, operator contact with a first input control of an input control console coupled to the system. The processor may also be configured to receive an input representing a commanded motion of the device at the first input control, and to execute the commanded motion when the processor determines that the operator is in contact with the first input control and affect the commanded motion when the processor determines that the operator is not in contact with the first input control.

Consistent with some embodiments, a method of operating a device includes determining, by a control unit using one or more sensors, whether an operator is in contact with a first input control of an input control console. The method also includes receiving an input representing a commanded motion of the device at the first input control. The method also includes executing the commanded motion when the control unit determines that the operator is in contact with the first input control and affect the commanded motion when the control unit determines that the operator is not in contact with the first input control.

Consistent with some embodiments, a non-transitory machine-readable medium comprising a plurality of machine-readable instructions which when executed by one or more processors associated with a device are adapted to cause the one or more processors to perform a method. The method includes determining, by a control unit using one or more sensors, whether an operator is in contact with a first input control of an input control console. The method also includes receiving an input representing a commanded motion of the device at the first input control. The method also includes executing the commanded motion when the processor determines that the operator is in contact with the first input control and affect the commanded motion when the processor determines that the operator is not in contact with the first input control.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 2A is a simplified diagram of a medical instrument system according to some embodiments.

Figure 1:
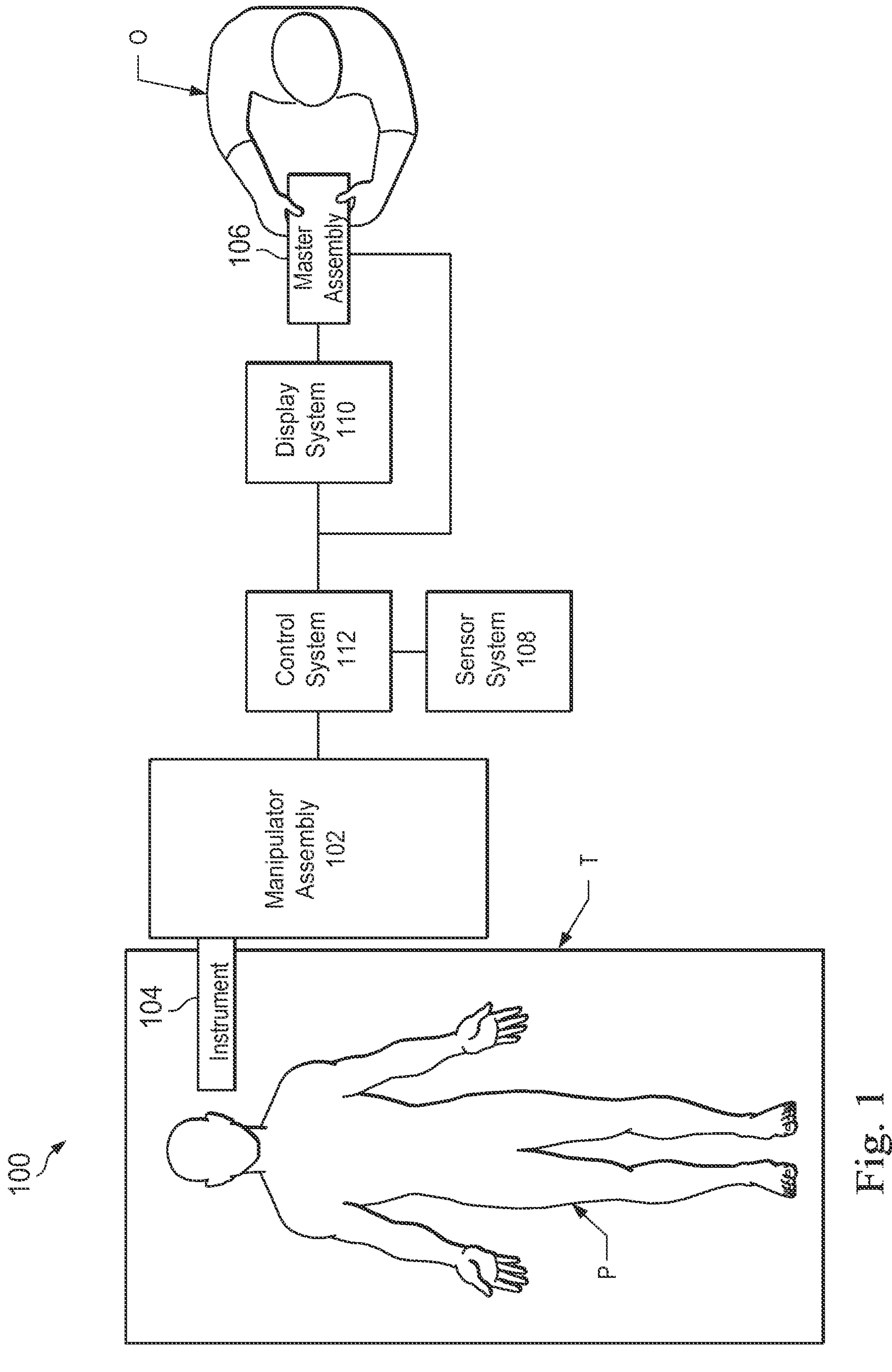
FIG. 1 is a simplified diagram of a teleoperated medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a manipulator assembly 102 for operating a medical instrument 104 in performing various procedures on a patient P. Manipulator assembly 102 is mounted to or near an operating table T. A master assembly 106 allows an operator O (e.g., a surgeon, a clinician, a physician and/or other healthcare provider) to view the interventional site and to control manipulator assembly 102.

Master assembly 106 may be located at a physician's console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure) and a manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

In some embodiments, teleoperated medical system 100 may include more than one manipulator assembly and/or more than one master assembly. The exact number of manipulator assemblies will depend on the surgical procedure and the space constraints within the operating room, among other factors. Master assembly 106 may be collocated or they may be positioned in separate locations. Multiple master assemblies allow more than one operator to control one or more manipulator assemblies in various combinations.

FIG. 2A is a simplified diagram of a medical instrument system 200 according to some embodiments. Medical instrument system 200 includes elongate device 202, such as a flexible catheter, coupled to a drive unit 204. Elongate device 202 includes a flexible body 216 having proximal end 217 and distal end or tip portion 218.

Figure 2B:
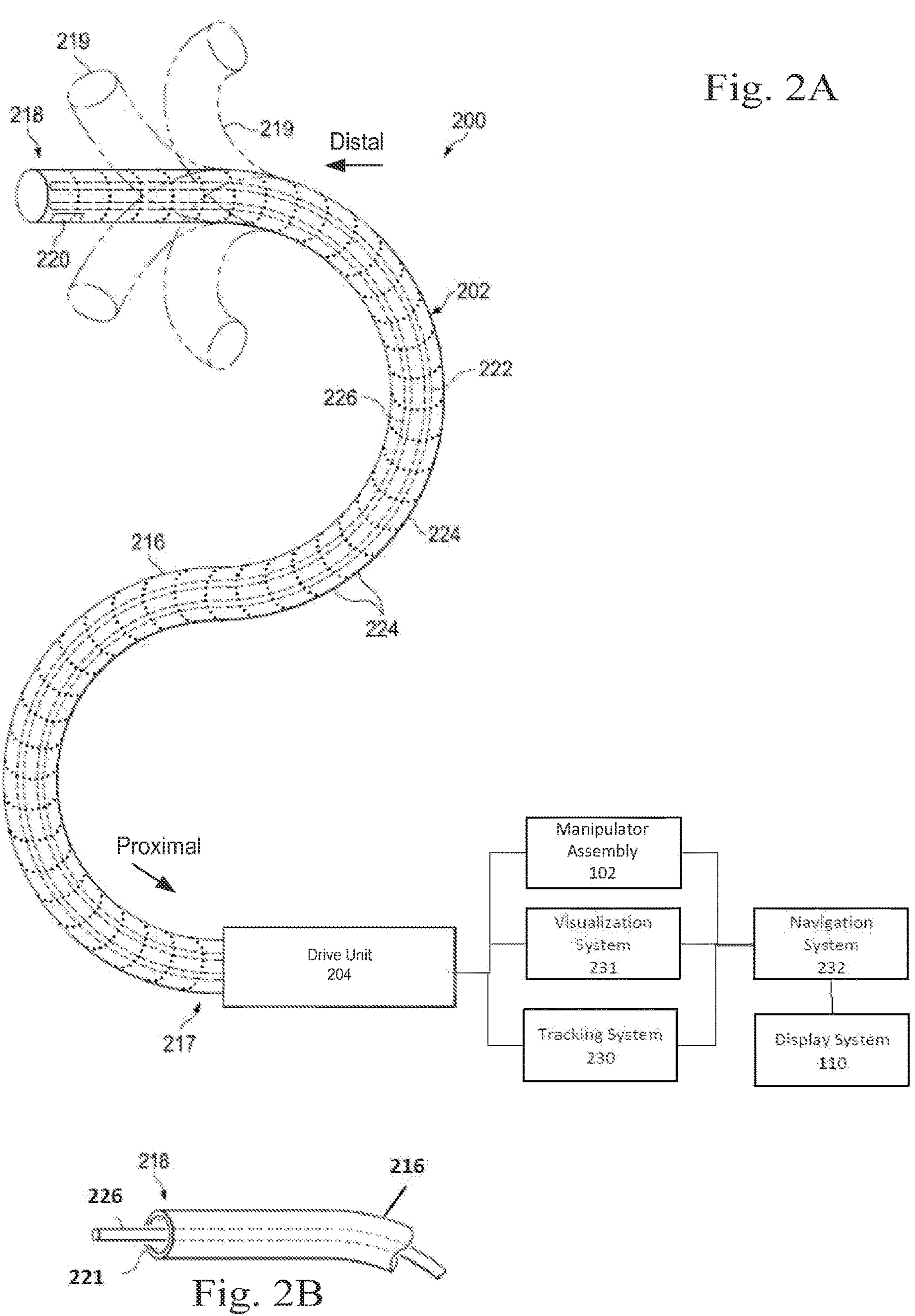
FIG. 2B is a simplified diagram of a medical instrument with an extended medical tool according to some embodiments.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (disclosing "Articulated Surgical Instrument for Performing Minimally Invasive Surgery with Enhanced Dexterity and Sensitivity") and U.S. Pat. No. 9,259,274 (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. Pat. No. 9,452,276 (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some examples, medical instrument system 200 may be teleoperated within medical system 100 of FIG. 1. In some embodiments, manipulator assembly 102 of FIG. 1 may be replaced by direct operator control.

Figure 3A:
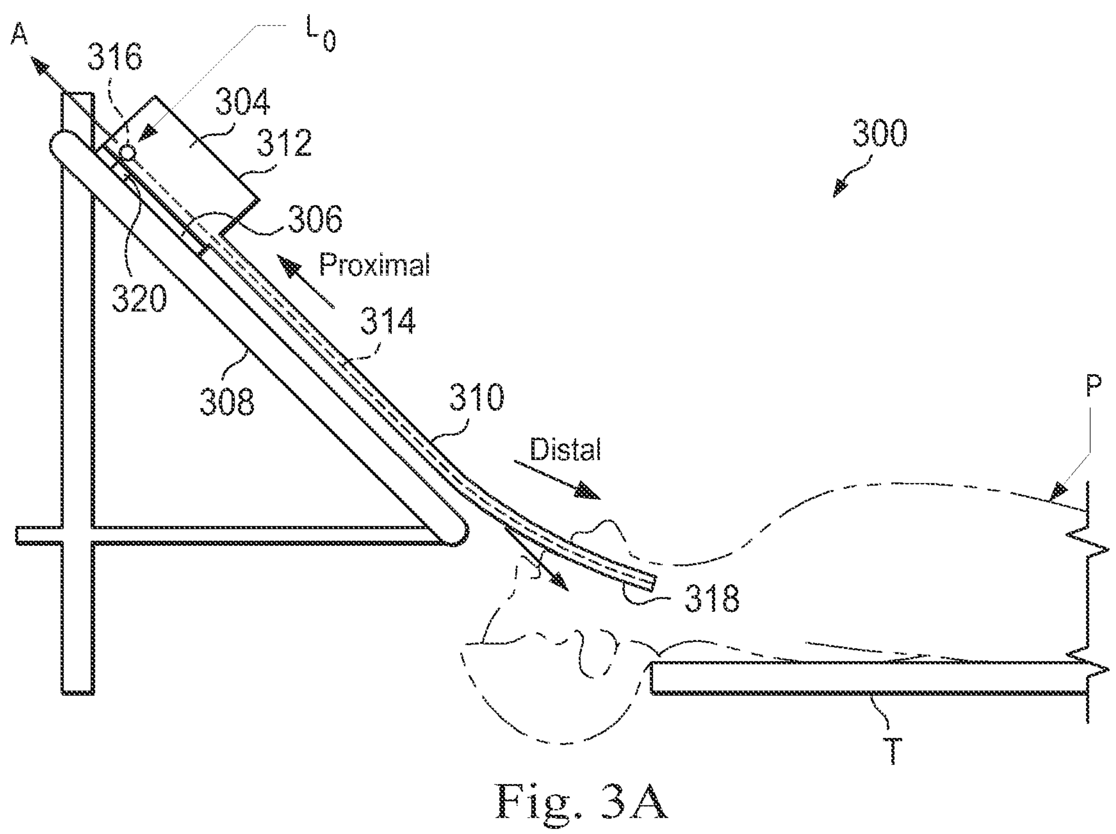
FIGS. 3A and 3B are simplified diagrams of side views of a patient coordinate space including a medical instrument mounted on an insertion assembly according to some embodiments.
Figure 3B:
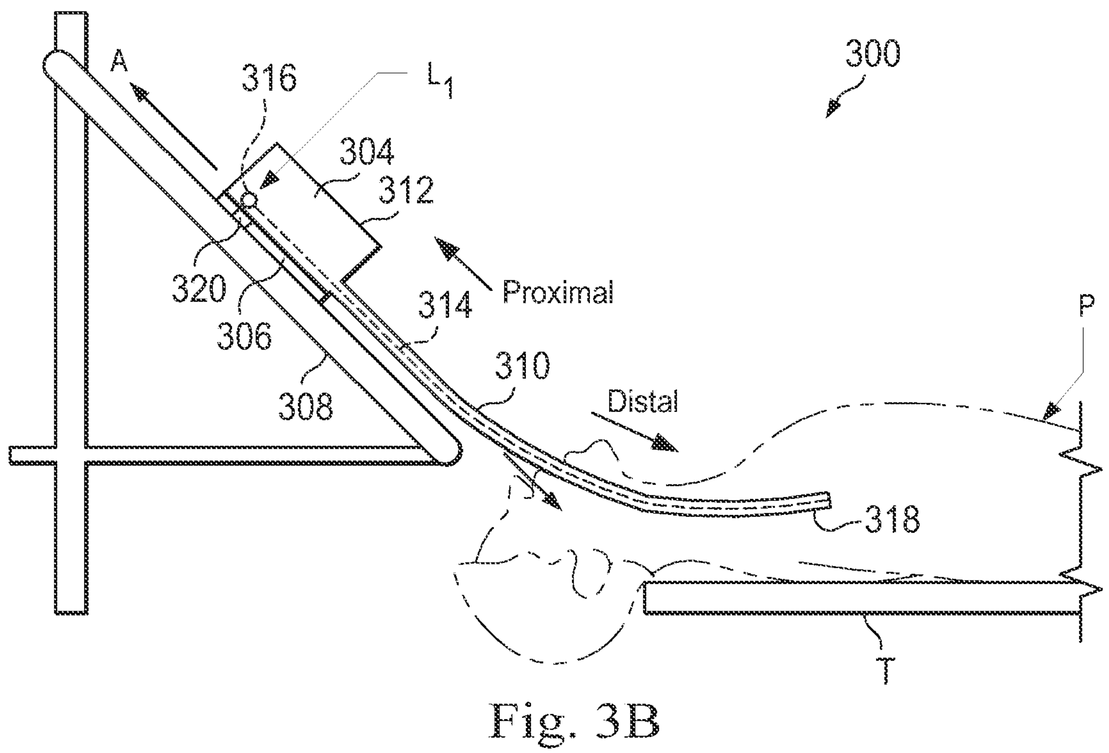

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on platform 302. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308. Elongate device 310 is coupled to an instrument body 312. Instrument body 312 is coupled and fixed relative to instrument carriage 306. A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. With this retracted position of instrument body 312 and instrument carriage 306, distal end 318 of elongate device 310 may be positioned just inside an entry orifice of patient P. In FIG. 3B, instrument body 312 and instrument carriage 306 have advanced along the linear track of insertion stage 308 and distal end 318 of elongate device 310 has advanced into patient P.

Control of a flexible elongate device such as elongate device 202 having flexible body 216, elongate device 310, and/or a flexible catheter often involves the simultaneous control of multiple degrees of freedom. In some examples, to control insertion and/or retraction of the elongate device and correspondingly an insertion depth of the distal end of the elongate device, such as distal end 218 and/or 318, one or more actuators, such as the one or more actuators controlling the position of instrument carriage 306 along insertion stage 308, are used. Commands to the one or more actuators may be received from operator O using a single degree of freedom input control, such as a lever, joystick, and/or the like. In some examples, to control the steering of the distal end, the steering unit for the distal end, such as drive unit 204, is provided with both pitch and yaw instructions. The pitch and yaw instructions may be received from operator O using a two-degree of freedom input control, such as a joystick. Because control of the elongate device typically includes concurrently providing insertion and/or retraction instructions along with steering instructions, the input controls for insertion and/or retraction and steering are typically separate from each other.

For certain procedures, the use of levers and/or joysticks as the input controls for the elongate devices of FIGS. 2A, 3A, and/or 3B can be less than ideal. This is because levers and joysticks are input controls that have a finite length of travel, which are often disproportionately short relative to the length of insertion travel and/or the range of steering necessary to access certain anatomy. Thus, use of the levers and/or joysticks as positional input devices that provide a limited insertion depth, pitch setting, and/or yaw setting can be inadequate. Input controls with a finite length of travel are typically used as velocity input devices where either movement of the input control either specifies three velocity settings (reverse, idle, and forward) for switch-type input controls or variable velocity settings for proportional type input controls. However, velocity-based control of the insertion depth, pitch setting, and/or yaw setting is often unsatisfactory for high-precision manipulation of the elongate device as the control of the velocity of the distal end does not generally intuitively correspond with desires to make small high-precision changes in the insertion depth, pitch setting, and/or yaw setting, which is typically required for teleoperated minimally invasive medical procedures.

Alternatively, input controls offering an infinite length of travel can be used as input controls for the elongate device when accessing certain anatomy. Input controls with an infinite length of travel correspond to input controls that allow continued movement of the inputs controls in a particular direction where no stop, such as a mechanical stop, restricts further movement. One example of a one degree of freedom input control with an infinite length of travel is a scroll wheel, which may be spun unendingly in either direction. One example of a multiple-degree of freedom input control with an infinite length of travel is a track ball, which may be spun unendingly about any number of axes, which in practice may be decomposed into combinations of a left and right rotation, a forward and back rotation, and a spin in place rotation. Other examples, of input controls that support an apparent infinite length of travel are input controls that support directional swipes without movement of the input control. Examples of directional swipe input controls are touch pads, touch screens, and/or the like.

Figure 4A:
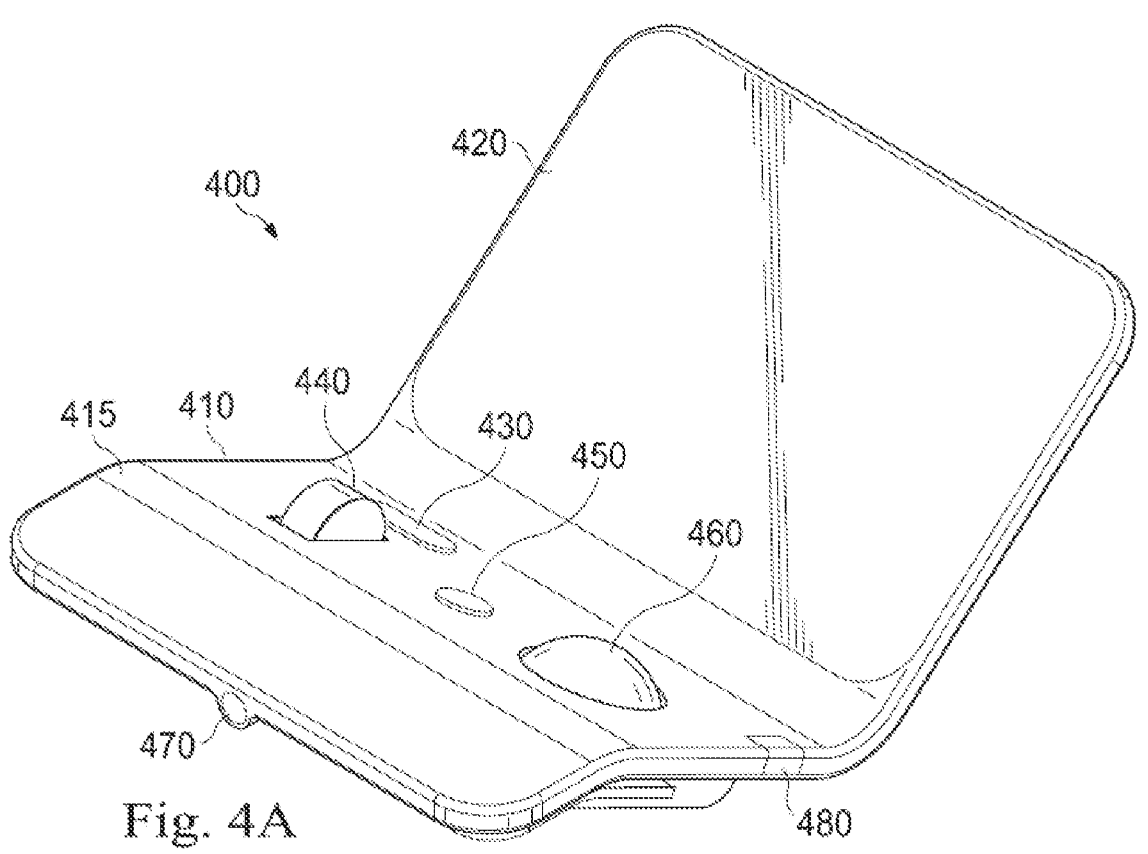
FIGS. 4A and 4B are simplified perspective diagrams of an input control console according to some embodiments.
Figure 4B:
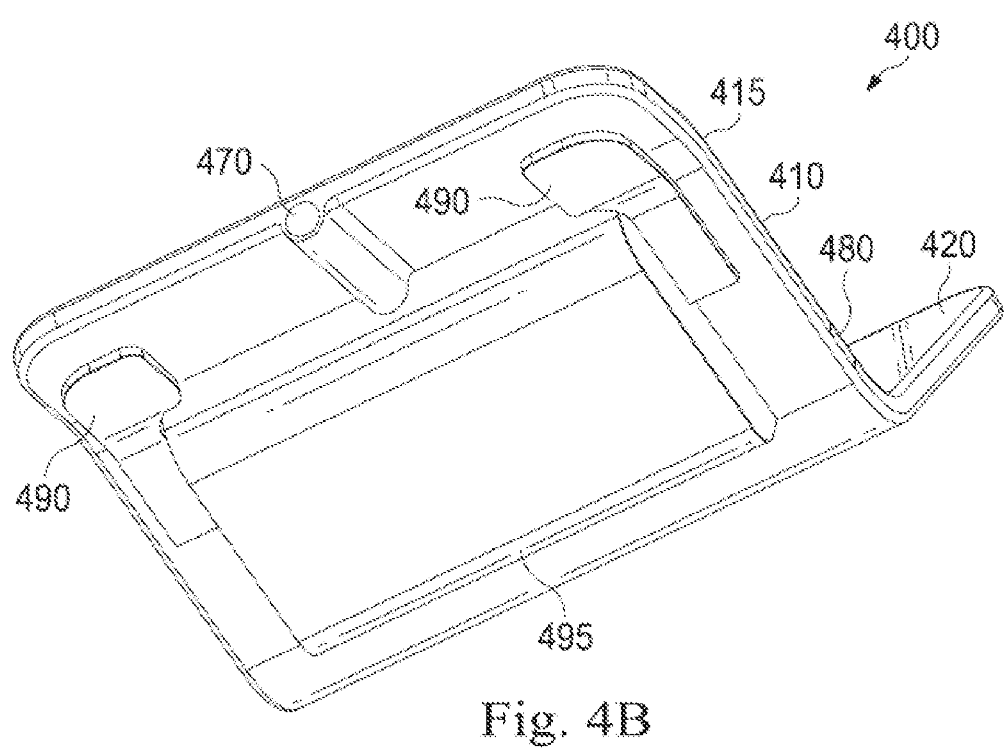

FIGS. 4A and 4B are simplified perspective diagrams of another input control console 400 according to some embodiments. FIG. 4A shows a top view of input control console 400 and FIG. 4B shows a bottom view of input control console 400. A top surface of input control console 400, further includes various input controls including a camera cleaning button 430, an insertion/retraction control 440, a passive control button 450, and a steering control 460. Although FIGS. 4A and 4B show configurations of the various input controls for an elongate device, it should be understood that input control console 400 can control any variety of instruments and devices and the exact placement, orientation, relative-positioning, and/or the like of the various input controls are exemplary only. It is understood that other configurations of input controls, different numbers of input controls, and/or the like are possible. In some embodiments, input control console 400 is suitable for use as a patient-side input control unit for the elongate device and may, for example, be mounted in proximity to insertion stage 308.

Although not shown in FIGS. 4A and 4B, input control console 400 may optionally include one or more circuit boards, logic boards, and/or the like that are usable to provide power, signal conditioning, interface, and/or other circuitry for input control console 400. In some examples, the one or more circuit boards, logic boards, and/or the like are useable to interface input control console 400 and its various input controls to a control unit for the elongate device. In some examples, the control unit of the elongate device corresponds to the control device of master assembly 106, control system 42, and/or the like. In some examples, the one or more circuit boards, logic boards, and/or the like may include memory and one or more one or more processors, multi-core processors, field programmable gate arrays (FPGAs), application specific integrated circuits (ASICs), and/or the like. In some examples, the memory may include one or more types of machine-readable media. Some common forms of machine-readable media may include floppy disk, flexible disk, hard disk, magnetic tape, any other magnetic medium, CD-ROM, any other optical medium, RAM, PROM, EPROM, FLASH-EPROM, any other memory chip or cartridge, and/or any other medium from which a processor or computer is adapted to read.

In some examples, insertion/retraction control 440 is a single degree of freedom infinite length of travel input control providing infinite length of travel along a first axis usable by the operator to control the insertion depth of the distal end of the elongate device. Insertion/retraction control 440 is depicted as a scroll wheel, however, other types of input controls, including non-infinite length of travel input controls, are possible. In some examples, scrolling of the scroll wheel forward away from the operator increases the insertion depth (insertion) of the distal end of the elongate device and scrolling of the scroll wheel backward toward the operator decreased the insertion depth (retraction) of the distal end of the elongate device. In some examples, insertion/retraction control 440 is usable by the operator to move instrument carriage 306 in and out along insertion stage 308 in order to control the insertion depth of distal end 318.

When insertion/retraction control 440 is an infinite length of travel input control, operating insertion/retraction control 440 in a position-specifying mode allows the operator to exercise precise insertion depth control of the distal end of the elongate device over the full length of travel of the elongate device. In some examples, movement of insertion/retraction control 440 may be detected by the one or more circuit boards, logic boards, and/or the like of input control console 400 using one or more encoders, resolvers, optical sensors, hall effect sensors, and/or the like (not shown). In some examples, feedback applied via one or more electromagnetic actuators, and/or the like may optionally be used to apply haptic feedback to insertion/retraction control 440. In some examples, a scale factor between an amount of movement of insertion/retraction control 440 and an amount of insertion and/or retraction movement by the elongate device is adjustable by the operator and/or control software of the elongate device so that an insertion/retraction velocity of the elongate device relative to an angular velocity of insertion/retraction control may be adjusted to allow both fast insertion and retraction when advantageous and slower more precise insertion and retraction when greater control precision is desired. In some embodiments, insertion/retraction control 440 may optionally be touch sensitive (e.g., via capacitive touch detection) and/or have pressure sensitivity so that input control console 400 is able to differentiate between intended movement of insertion/retraction control 440 by the operator from inadvertent movement due to accidental contact, dropping of input control console 400, and/or the like.

In some examples, steering control 460 is a multi-degree of freedom infinite length of travel input control providing infinite length of travel about any number of axes, which in practice may be decomposed into combinations of a left and right rotation, a forward and back rotation, and a spin in place rotation. Steering control 460 is depicted as a track ball, however, other types of input controls, including non-infinite length of travel input controls, are possible. Steering control 460 is usable by the operator to concurrently control both the pitch and yaw of the distal end of the elongate device. In some examples, components of the track ball rotation in the forward and back directions may be used to control a pitch of the distal end of the elongate device and components of the track ball rotation in the left and right directions may be used to control a yaw of the distal end of the elongate device. In some examples, other rotational components of the track ball may be used to control pitch and/or yaw with the operator being optionally able to control whether the direction of rotation is normal and/or inverted relative to the direction applied to the steering (e.g., rotate forward to pitch down and backward to pitch up versus backward to pitch down and forward to pitch up). In some examples, steering control 460 is usable by the operator to manipulate the distances each of the cables extending between the proximal and distal ends of the elongate device are pushed and/or pulled.

When steering control 460 is an infinite length of travel input control, operating steering control 460 in a position-specifying mode allows the operator to exercise precise steering of the distal end of the elongate device in both pitch and yaw concurrently so as to achieve precise control over an orientation of the distal end. In some examples, movement of steering control 460 may be detected by the one or more circuit boards, logic boards, and/or the like of input control console 400 using one or more encoders, resolvers, optical sensors, hall effect sensors, and/or the like (not shown). In some examples, feedback applied to the one or more electromagnetic actuators and/or the like may optionally be used to apply haptic feedback to steering control 460. In some examples, a scale factor between an amount of movement of steering control 460 and an amount of pitch and/or yaw imparted to the distal end of the elongate device is adjustable by the operator and/or control software of the elongate device. In some embodiments, steering control 460 may optionally be touch sensitive (e.g., via capacitive touch detection) and/or have pressure sensitivity so that input control console 400 is able to differentiate between intended movement of steering control 460 by the operator from inadvertent movement due to accidental contact, dropping of input control console 400, and/or the like.

In some embodiments, input control console 400 may optionally support a lock mode of operation. In the lock mode of operation, when input control console 400 detects loss of affirmative contact by the operator with insertion/retraction control 440 and/or steering control 460, such as via the capacitive touch or pressure sensitive features of insertion/retraction control 440 and/or steering control 460, a rigidity of the elongate device may increase and/or insertion and/or retraction may be prevented. In the lock mode, a position and/or orientation of the distal end of the elongate device is maintained at the position and/or orientation detected before loss of affirmative contact was detected.

Input control console 400 is provided as a representative example of possible input control consoles for a computer-assisted medical device, such as the elongate device of FIGS. 1-3B. Additional variations and/or configurations of input control consoles may be found in International Patent Application No. PCT/US2017/039808, filed on Jun. 28, 2017 and entitled "Systems and Methods of Steerable Elongate Device," and concurrently filed and co-owned U.S. Provisional Patent Application 62/539,467 (disclosing "Systems and Methods of Steerable Elongate Device"), both of which are incorporated by reference herein in their entirety.

Figure 5:
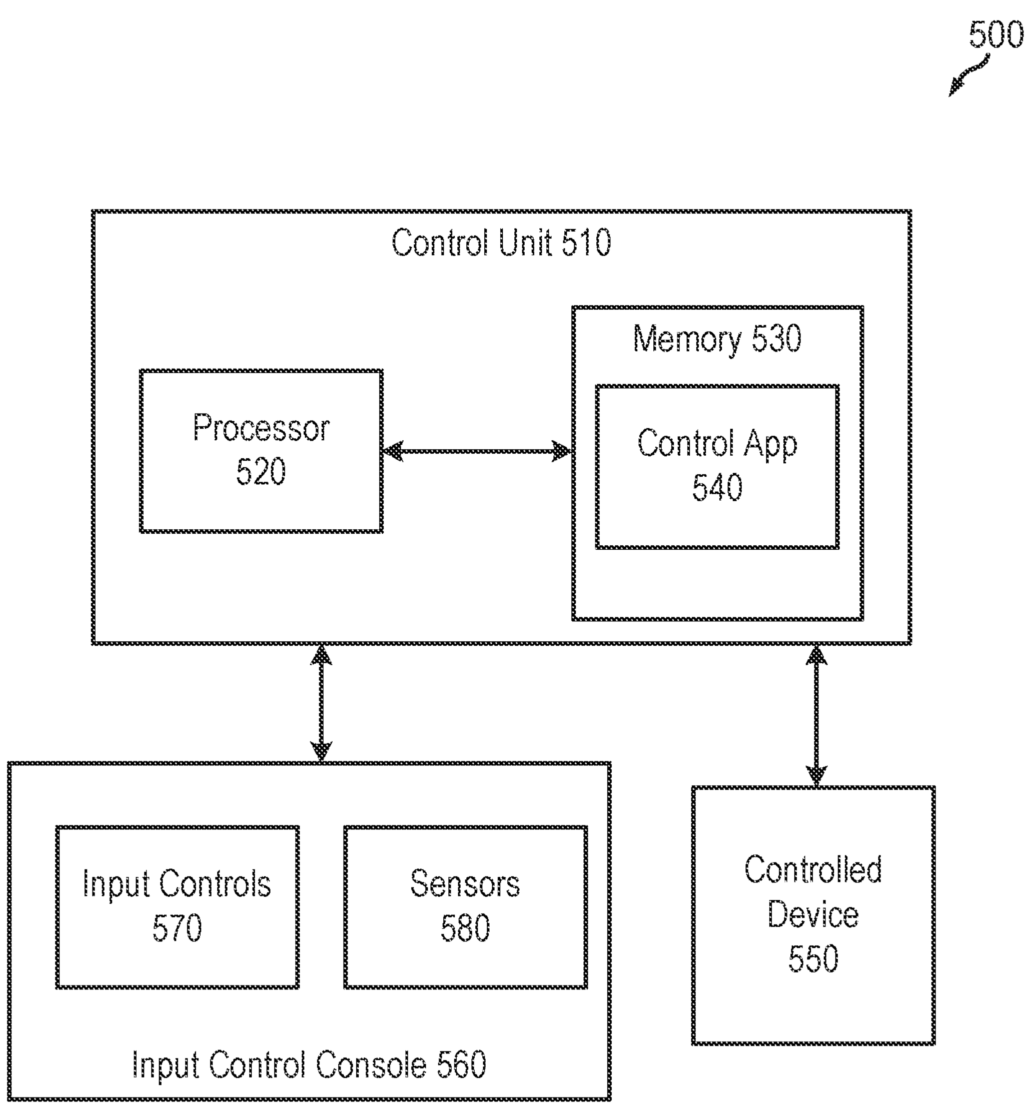
FIG. 5 is a simplified diagram of a control system according to some embodiments.

FIG. 5 is a simplified diagram of a control system 500 according to some embodiments. In some embodiments, control system 500 may correspond to one or more portions of sensor system 108, display system 110, and/or control system 112 of FIG. 1. As shown in FIG. 5, control system 500 includes a control unit 510. Control unit 510 includes a processor 520 coupled to memory 530. Operation of control unit 510 is controlled by processor 520. And although control unit 510 is shown with only one processor 520, it is understood that processor 520 is representative of one or more central processing units, multi-core processors, microprocessors, microcontrollers, digital signal processors, field programmable gate arrays (FPGAs), application specific integrated circuits (ASICs), and/or the like in control unit 510. Control unit 510 may optionally be implemented as a stand-alone subsystem and/or board added to a computing device or as a virtual machine. In some embodiments, control unit 510 may optionally be included as part of an operator workstation (not shown) and/or operated separately from, but in coordination with the operator workstation.

Memory 530 is used to store software executed by control unit 510 and/or one or more data structures used during operation of control unit 510. Memory 530 includes one or more types of machine-readable media. Some common forms of machine-readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 530 includes a control application 540 that supports autonomous, semiautonomous, and/or teleoperated control of a controlled device 550 coupled to control unit 510. In some examples, controlled device 550 is a computer-assisted medical device, such as the elongate device of FIGS. 1-3A. Control application 540 includes one or more control modules for controlling the drive units and/or actuators of controlled device 550 to control, for example, an insertion depth of controlled device 550, steer controlled device 550, operate an instrument at the distal end of controlled device 550, and/or the like. Control application 540 may also include one or more modules and/or application programming interfaces (APIs) for receiving position, motion, and/or other sensor information from controlled device 550. In some embodiments, one or more registration markers, fiducial markers, and/or the like mounted on controlled device 550 may be tracked using one or more tracking sensors, such as an imaging device, a shape sensor, and/or the like.

Control application 540 further includes one or more modules for interfacing with an input control console 560 being operated by an operator, such as operator O. In some examples, input control console 560 is consistent with input control console 400. Control application 540 receives control inputs from one or more input controls 570, which may include one or more of camera cleaning button 430, insertion/retraction control 440, passive control button 450, steering control 460, emergency stop button 470, and/or the like. Control application 540 further includes one or more modules for sending status information, images, haptic feedback, and/or the like to input control console 560. In some examples, the status information, images, and/or the like may be sent to input control console 560 for display on an integrated display screen, such as screen 420.

Control application 540 further includes one or more modules for interfacing with one or more sensors 580 of input control console 560. In some examples, the one or more sensors 580 may include one or more ways to detect whether commands from the one or more input controls 570, such as insertion, retraction, and/or steering commands are being received via affirmative control by the operator using the one or more input controls 570 or from inadvertent movement of the one or more input controls 570, such as due to inadvertent contact, dropping of input control console 510, tipping over of input control console 510, and/or the like.

Control unit 510 is coupled to controlled device 550 and input control console 560 via an input/output (I/O) interface (not shown) that may include one or more drivers, signal conditioners, receivers, ports, and/or the like. The I/O interface may optionally include one or more cables, connectors, ports, and/or buses, and it may optionally further include one or more networks with one or more network switching and/or routing devices. In some examples, the I/O interface may optionally include wireless interfaces.

And although control application 540 is depicted as a software application, control application 540 may be implemented using hardware, software, and/or a combination of hardware and software.

Operation of controlled device 550 raises some safety concerns regarding safety to controlled device 550 and/or a material, such as tissue of a patient, being manipulated by controlled device 550. In some examples, these safety concerns may be increased when controlled device 550 is controlled robotically and/or remotely, such as by using control unit 510 and input control console 560, and/or when one or more infinite length of travel input controls, such as the scroll wheel and/or trackball of an input control console like input control console 400. In some examples, these safety concerns may be suitably mitigated by providing haptic feedback to the operator, displaying live images and/or tracking data to the operator (e.g., using screen 420), and/or the like. The use of these types of feedback, however, is generally limited to cases where the operator is actively engaged with and using input control console 560, but may be of limited efficacy when the operations being commanded using input control console are due to inadvertent motion of the one or more input controls 570 due to accidental contact with the one or more input controls 570, dropping and/or tipping of input control console 560, and/or the like. Accordingly, improved safety in the operation of controlled device 550 may be obtained by using the one or more sensors 580 to differentiate between affirmative and desired control of the one or more input controls 570 by the operator and inadvertent control due to other causes.

Approaches to providing this improved safety are discussed in the context where controlled device 550 is an elongate device, such as the elongate device of FIGS. 1-3A, and input control console 560 is similar to input control console 400 and includes an insertion/retraction control, such as insertion/retraction control 440, and a steering control, such as steering control 460. However, it is understood that the improved safety features may be easily adaptable to other controlled devices and/or other input control consoles with similar and/or different input controls, including control of multiple devices in insert/retract, steering, roll, end effector actuation, and/or the like using the same control console with multiple input controls or multiple control consoles with multiple input controls.

In some embodiments, controlling the motion of an elongate device may involve three types of motion: insertion motion where the distal end of the elongate device is advanced further into a material or passageway (a proximal to distal direction), retraction motion where the distal end of the elongate device is retreated along the path of the elongate device body (a distal to proximal direction), and steering motion where the distal end of the elongate device is bent in pitch or yaw. In some examples, the insertion and retraction may be controlled using a combined insertion/retraction control and the steering may be controlled by a separate steering control. In one example, detection of affirmative contact with the insertion/retraction control can allow for insertion/retraction control while detection of affirmative contact with the steering control can allow for steering control. Of the three types of motion, the insertion motion may be subject to stricter safety procedures depending on a type of procedure to be performed and/or anatomy the procedure is performed within but safety procedures may also be necessary for retraction or steering based on anatomy and procedure type. In some examples, these stricter safety procedures may include detecting affirmative contact with both the insertion/retraction control and the steering control by the operator before allowing further insertion motion, but just affirmative contact with the insertion/retraction control before allowing retraction and just affirmative contact with the steering control before allowing steering.

In some embodiments, controlling the motion of the elongate device may involve one or more additional types of motion. In some examples, the one or more additional types of motion may include one or more of roll, rotation of a distal end of the elongate device, articulation of a distal end of the elongate device independent of the insertion and/or steering control; actuation of an end effector at the distal end of the elongate device, and/or the like. In some examples, the one or more additional types of motion may be controlled using one or more additional input controls. In some examples, the control console may include three or more input controls subject to the safety features described herein.

Several techniques are available for detecting affirmative contact with the insertion/retraction control and/or the steering control by the operator. In some examples, one or more sensors associated with the insertion/retraction control and/or the steering control may be used to detect actual operator contact with the insertion/retraction control and/or the steering control. In some examples, the one or more sensors may be capacitive touch sensors associated with, for example, the scroll wheel and/or track ball, that are able to differentiate between touch by the fingers of the operator and contact with foreign objects, including the floor, instruments, devices, tools, and/or the like. In some examples, the one or more sensors may be pressure sensors, such as a contact switch, strain gauge, and/or the like between the scroll wheel and/or track ball and the molding in which the scroll wheel and/or track ball sits and/or between the molding and the body of the input control console. When sufficient downward pressure on the scroll wheel and/or trackball are detected, such as by the fingers of the operator, affirmative contact may be detected.

In some embodiments, other types of operator detection sensors may be used. In some examples, one or more proximity sensors may be used to detect the presence of fingers and/or hands above and/or near the input controls and/or to detect fingers, hands, wrists, and/or fore arms above or near the upper surface of the input control console. In some examples, the one or more proximity sensors may include one or more ultrasonic sensors, one or more vision sensors, one or more light walls, and/or the like. In some examples, data from the proximity sensors may be evaluated using one or more pattern and/or image processing techniques to differentiate the operator from other foreign objects in the vicinity of the input control console. In some examples, one or more pressure and/or touch sensors located in a wrist rest in front of each of the input controls may be used to detect the presence of a wrist and a corresponding hand near the one or more input controls. In some examples, the input control console may optionally include one or more accelerometers to determine whether recent sudden motion of the input control console has occurred, the input control console is not oriented in a sufficiently upright orientation (e.g., such as the orientations permitted by the one or more paddle levers 490 of input control console 400), and/or the like.

In some embodiments, one or more affirmative contact activities may be used to detect affirmative contact of the operator with the one or more input controls. In some examples, the one or more pressure sensors associated with the input controls may be used to detect a wake-up activity, such as a double-press/double click of the corresponding input control, a press and hold for a minimum duration of the corresponding input control, and/or the like. In some examples, the wake-up activity may be used as a precursor action before allowing motion indicated by the corresponding input control to be passed on to the controlled device. In some examples, other wake-up like precursor activities may include one or more of a minimum affirmative contact period (e.g., 0.05 to 0.5 seconds or more and/or other period that does not place an unreasonable delay in the operator being able to begin control of the controlled device after the operator makes affirmative contact), a minimum affirmative contact period ((e.g., 0.05 to 0.5 seconds or more and/or other period that does not place an unreasonable delay in the operator being able to begin control of the controlled device after the operator makes affirmative contact) without motion of the corresponding input control above a threshold, a wiggle or other specified pattern in the corresponding input control, engagement of a secondary control (e.g., a foot pedal), and/or the like before allowing use of the corresponding input control.

In some embodiments, one or more safety operational limits may be used to further protect from false positives in the detection of affirmative contact by the operator. In some examples, an upper limit on the allowed velocity of the movement of the controlled device is implemented. In some examples, the safety operational limits may include a scale up period of (e.g., 0.2 to 2 seconds or more) when a corresponding input control is first used so that the amount of motion that results from operation of the corresponding input control is initially reduced so as to avoid significant movement of the controlled device due to inadvertent contacts with the corresponding input control. In some examples, the scale may include scaling of a ratio between an amount of movement in the corresponding input control and an amount of movement of the controlled device, scaling a maximum allowed velocity of the movement of the controlled device, and/or the like.

According to some embodiments, combinations of one or more of the previously discussed safety options may be used to detect affirmative contact with the one or more input controls by the operator. In some examples, the combination may include detection of affirmative contact by each of the available methods, a weighted combination of likelihood of affirmative contact determined using each of the available methods, a voting mechanism, and/or the like. As but some of many possible examples, an accelerometer detecting input control console orientation may be used in conjunction with one or more capacitive touch sensors associated with one or more input controls, one or more capacitive touch sensors associated with one or more input controls may be used in conjunction with one or more wrist detection sensors, one or more capacitive touch sensors associated with one or more input controls may be used in conjunction with one of the affirmative contact activities, one or more capacitive touch sensors associated with one or more input controls may be used in conjunction with one of the safety operational limits, and/or the like.

In some embodiments, each of the minimum durations, contact periods, scaling periods, upper limits, scaling ratios, maximum allowed velocities, and/or the like are configurable. In some examples, their values may be set by interacting via a display screen, such as screen 420. In some examples, their values may be set by importing them using a data port, such as data port 480. In some examples, their values may be set based on an operator, a patient, a procedure, and/or the like.

Figure 6:
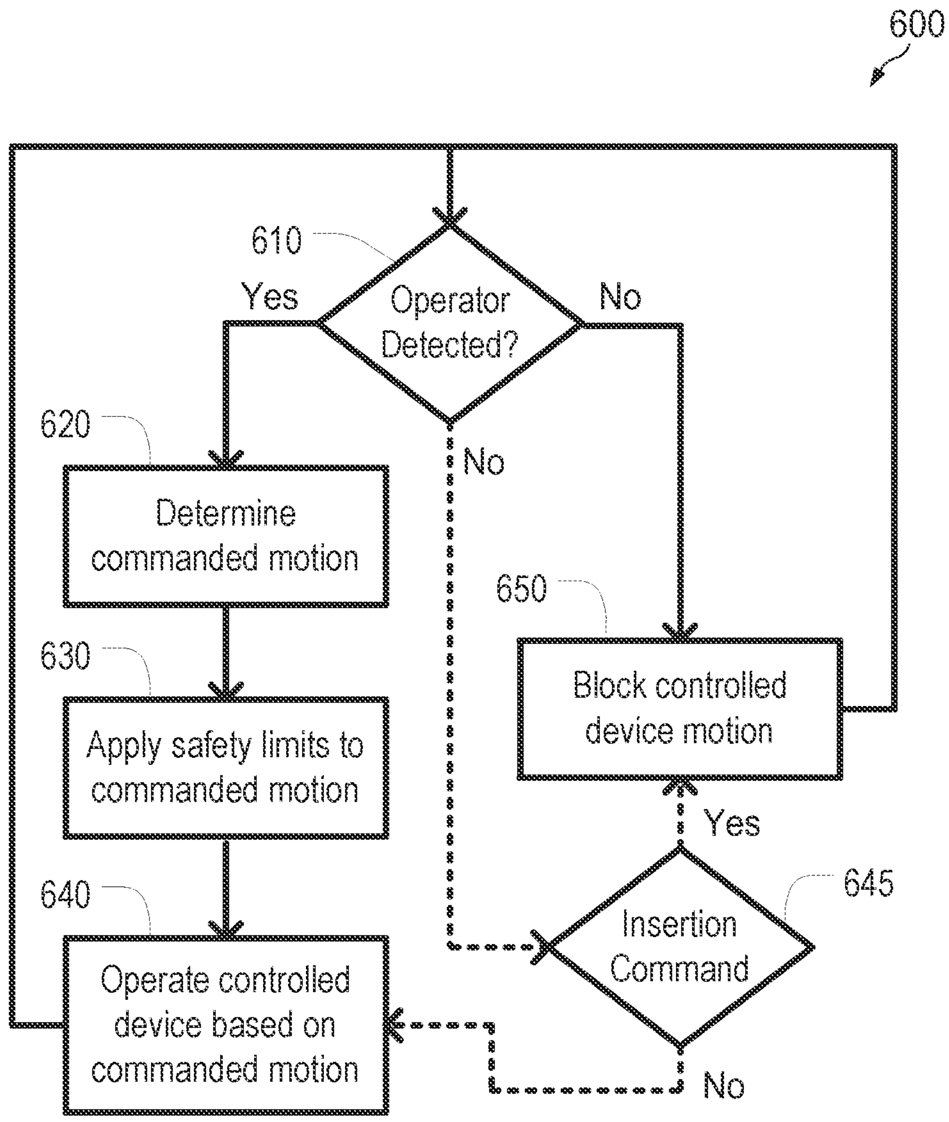
FIG. 6 is a simplified diagram of a method of operating a controlled device subject to safety features according to some embodiments.

FIG. 6 is a simplified diagram of a method 600 of operating a controlled device subject to safety features according to some embodiments. One or more of the processes 610-650 of method 600 may be implemented, at least in part, in the form of executable code stored on non-transitory, tangible, machine-readable media that when run by one or more processors (e.g., the processor 520 in control unit 510) may cause the one or more processors to perform one or more of the processes 610-650. According to some embodiments, the order in which processes 610-650 are performed may optionally vary from the order implied by the diagram of FIG. 6. In some examples, process 610 may operate in parallel with processes 620-640 to stop operation of the controlled device and move to process 650 before completing further commanded motion. In some examples, processes 620-640 may optionally be performed concurrently or in any order. In some examples, process 630 is optional and may be omitted. In some examples, method 600 may include one or more additional processes that may occur before, in between, and/or concurrently with processes 610-650. For the purposes of illustration, method 600 is described in a context where the controlled device is a computer-assisted medical device, such as the elongate device of FIGS. 1-3B, using an input control console, such as input control console 400 having an insertion/retraction control and a steering control.

At a process 610, affirmative contact by a human operator with one or more input controls is detected. In some examples, one or more sensors associated with the insertion/retraction control and/or the steering control may be used to detect actual human operator contact with the insertion/retraction control and/or the steering control. In some examples, the one or more sensors may be capacitive touch sensors, pressure sensors (e.g., contact switches, strain gauges, and/or the like), and/or the like. In some examples, one or more proximity sensors (e.g., one or more ultrasonic sensors, vision sensors, light walls, and/or the like) may be used to detect operator proximity to the input controls. In some examples, one or more wrist detection sensors (e.g., capacitive touch, pressure, and/or similar sensors) in a wrist rest may be used to detect operator proximity to the input controls. In some examples, one or more accelerometers may be used to detect whether an orientation of the input console is within operational limits, whether sudden recent motion has occurred, and/or the like. In some examples, one or more affirmative contact activities (e.g., double presses, press and hold for a minimum duration, sustained operator contact for a minimum duration, operator contact with minimal motion for a minimum duration, engagement of a secondary control, and/or the like) may be used as a precursor before confirming detection of affirmative contact by the operator. In some examples, a combination of one or more of these approaches may be used to determine whether affirmative contact by the operator has occurred. In some examples, the combination may include may include detection of affirmative contact by each of the available methods, a weighted combination of likelihood of affirmative contact determined using each of the available methods, a voting mechanism, and/or the like.

Affirmative contact may be determined by any of several different methods or patterns. In some examples, affirmative contact may require a persistent or ongoing detected contact for a preset period of time. For example, if the preset period of time were 0.5 seconds, then the control system would detect affirmative contact at 610 only when the detected contact is persistent or ongoing for at least 0.5 seconds. The preset period of time may be set at any suitable value, and may in some examples, be in a range from about 0.2 to 1.5 seconds, although other preset time periods are contemplated. In another example, affirmative contact may require simultaneous contact of at least two input controls. For example, affirmative contact may be determined when the operator touches both a scrollwheel input control and a trackball input control at the same time. In some implementations, the simultaneous contact of at least two input controls may still include a time threshold as a preset period of time that the at least two input controls must be touched. In one example, the preset period of time may be smaller than the preset period of time for affirmatively contacting a single input control. In yet another example, affirmative contact may be determined when the control system detects repeated taps over a certain period of time. This may include, for example, determining affirmative contact when the input control is touched and untouched at least 3 times over a period of time, that may be established as a period of time in a range of about 0.5 to 2.5 seconds, although larger and smaller periods of time are contemplated. In yet another example, affirmative contact may be determined when the control system detects repeated quick taps or a double tap on the input control. In yet other examples, affirmative contact may be determined when the control system recognizes a finger "trace" on an input control. This may include detection of an area or shape of contact, and matching the area or shape of contact to pre-stored areas or shapes of contact. The pre-stored area or shape of contact may correspond to that of a portion of a curve of a fingertip, for example. Accordingly, the affirmative contact may be determined when the control system recognizes a finger trace that may be bigger than or shaped differently than may typically occur as a result of an accidental or inadvertent contact. In yet another example, affirmative contact may be found based on a recent user touch pattern. For example, if the user has been making voluntary repeated short contacts with an input control, the affirmative contact may be found based upon persistent contact for a short period of time, while if the user has not been making voluntary repeated short contacts with an input control, then the affirmative contact may be found based upon persistent contact for a longer period of time. Accordingly, in this embodiment, affirmative contact may be found based on a recent historical touch pattern. Yet other methods of determining affirmative contact are contemplated.

In some embodiments, the detection of affirmative contact by the operator may optionally depend on the type of motion to be performed by the controlled device as is discussed further below with respect to process 640. In some examples, affirmative contact with each of the input controls (e.g., both an insertion/retraction control and a steering control) should be detected before determining that there is affirmative contact by the operator. In some examples, affirmative contact with each of the input controls should be detected before determining that there is affirmative contact by the operator to allow insertion motion, but affirmative contact with just a corresponding input control should be detected before determining that there is affirmative contact by the operator to allow retraction motion and/or steering motion.

When affirmative contact by the operator is detected, motion using the one or more input controls is allowed beginning with process 620. When affirmative contact by the operator is not detected, motion using the one or more input controls is blocked using process 650. At the process 620, the commanded motion is determined. In some examples, operator activation of the one or more input controls (e.g., the insertion/retraction control and/or the steering control) is determined. In some examples, a corresponding amount of travel/position of the one or more input controls is determined and/or a corresponding velocity of the one or more input controls is determined. The corresponding amount of travel/position and/or velocity are used to determine appropriate commanded set points (e.g., position and/or velocity) for the motion to be commanded in the controlled device.

At the optional process 630, one or more safety limits are applied to the commanded motion determined during process 620. In some examples, the one or more safety limits may include a period of predetermined duration (e.g., 0.2 to 2 seconds or more) when a maximum amount of commanded motion is allowed. In some examples, the maximum amount of commanded motion (e.g., a maximum velocity limit) may be scaled up during the predetermined duration. In some examples, the one or more safety limits may include limitations on a scaling between the amount of input control movement and an amount of controlled device movement. In some examples, the scaling may be ramped up over a predetermined duration (e.g., 0.2 to 2 seconds or more).

The maximum velocity limit may be a velocity cap that limits velocity of the controlled device when the control system receives a commanded motion. Such a velocity cap may help mitigate the impact of an inadvertent touch or input by an operator's hand. For example, if an operator inadvertently hits or brushes up against an input device with his or her hand, the control system sensor may detect an operator, even though the input was inadvertent. The velocity cap may be set at a low value, such as zero velocity when no contact with an input device is detected. Then, when the initial contact is made and an operator is detected at process 610, the velocity cap may be increased. With continued detected contact, the velocity cap may continue to be increased until it reaches a maximum threshold, which may correspond to a level above or at a desirable working velocity. Once the contact with the input controls is interrupted, the velocity cap may be reset to the initial low value, which may be zero. Thus, if the input control were to be accidentally touched by an operator's hand or skin, the commanded motion would be applied at a very low velocity, resulting in minimal risk to patient anatomy. If the touch was intentional such that the user was actively actuating the input control, then the resulting movement would initially be restricted by the low velocity cap, and may ramp to a working velocity. This may appear to be relatively seamless to the operator.

In some implementations, the velocity cap may be maintained at a low level for the predetermined duration (e.g., 0.2 to 2 seconds or more), and then the velocity cap may ramp up toward the maximum threshold at a predetermined rate. For example, and without limitation, upon detecting an operator input at process 610 and determining a commanded motion at 620, the system may apply the velocity cap as the safety limit at process 630. For example, the limited velocity may ramp from zero velocity to be in a range of about 2 cm/second during the predetermined duration, and then may gradually increase after the predetermined period to the maximum velocity threshold. The maximum velocity threshold may be, for example and without limitation, in a range of about 4 cm-20 cm per second. The values presented herein are example values to aid understanding and are not intended to be limiting on the values contemplated in this disclosure. That is, larger and smaller caps and limits are contemplated. The velocity cap increase may be linear, exponential, stepped, some combination of these types, or other type of increases. Some velocity cap implementations may ramp during the predetermined duration from zero to a preset limit, while in other velocity cap implementations may ramp from 0 to the maximum velocity threshold. In some embodiments, the predetermined duration and the velocity cap may be applied only for insertion commanded motion, and may not apply for retraction commanded motion. In some alternative embodiments, the velocity limit can be applied to any commanded motion irrespective of degree of freedom or direction.

At a process 640, the controlled device is operated based on the commanded motion determined during process 620 and as optionally limited during process 630. In some examples, the commanded motion may include controlling an insertion depth of an elongate device, such as by controlling a position of an actuator, such as instrument carriage 306, in response to insertion and/or retraction commands received from the insertion/retraction control. In some examples, the commanded motion may include controlling a distal end of the elongate device, such as by controlling tension in one or more steering cables in the elongate device. In some examples, the commanded motion may be limited depending upon its type. In some examples, affirmative contact with each of the input controls (e.g., both an insertion/retraction control and a steering control) should be detected before applying any commanded motion to the controlled device. In some examples, affirmative contact with each of the input controls should be detected before applying any commanded insertion motion, but affirmative contact with just a corresponding input control should be detected before applying any commanded retraction motion and/or steering motion.

After applying the commanded motion, method 600 may return to process 610 to determine whether affirmative contact by the operator with the one or more input controls is still established.

At the process 650, motion of the controlled device is blocked. In some examples, when affirmative operator contact is no longer detected for one or more of the input controls, the controlled device may be transitioned to a lock mode. In the lock mode, insertion or retraction may be prevented (e.g., by stopping further movement of an instrument carriage, such as instrument carriage 306), and/or a rigidity of the elongate device may be increased (e.g., by increasing tension in the one or more steering cables) to prevent a change in bend of the distal end of the elongate device and/or further insertion. In some examples, the rigidity may be increased a varying amount depending on whether continuing bending motion of the distal end is detected. In yet other examples, the lock mode may decrease the rigidity of the elongate device (e.g., by decreasing tension in the one or more steering cables) so that the elongate device may be in a flexible, retractable condition, even while insertion and/or retraction and/or other motion is locked and therefore prevented.

In some implementations, the control system may apply different control profiles to different types of commanded motion (e.g., insertion, retraction, and steering). For example, since insertion of a device may increase a risk of puncture or injury to patient anatomy, insertion commanded motion may be controlled differently than retraction commanded motion. For example, in some embodiments, the lock mode may be applied to only certain types of commanded motion. That is, in some examples, the lock mode may apply to each type of commanded motion (e.g., insertion, retraction, and steering), while in other examples, the lock mode may apply just to one or more commanded motions, but not to other commanded motions, even when affirmative contact with one or both of the input controls is not detected. The dashed lines in FIG. 6 teach one such exemplary implementation, where the control system includes different motion permissions for different types of commanded motions. In the dashed line FIG. 6 example, the control system permits retraction motion but prevents insertion motion when an operator is not detected. Referring to FIG. 6, if at process 610, an operator is not detected, the control system may determine at process 645 whether the commanded motion is directed as an insertion command. If at process 645, the commanded motion is an insertion command, then the control system may block controller device motion at the process 650, as discussed herein. If however, at process 645 the commanded motion is not an insertion input, then the control system may allow the commanded motion to be carried out by the controlled device. In this example, if the commanded motion is a retraction motion, the control system would execute the commanded motion by retracting the elongate device. Such a system may be established when it is determined that a retraction motion, even if inadvertent, could, in some embodiments, provide limited or no safety risk to a patient. Although the example in FIG. 6 indicates that an insertion motion would be prevented, other implementations may prevent other motions, such as retraction or steering, while still permitting yet other commanded motions.

Some implementations apply yet other different control profiles to different types of commanded motion. In some implementations, these controls may be based upon the type of input controls. As described herein, some input controls are infinite length of travel devices, such as track balls and scroll wheels, among other devices. The motion permissions for these types of travel devices may be different for each type of commanded motion. For example, some a scroll wheels, trackballs, or similar devices may be constructed with enough mass and/or supported with minimal friction so that a force applied to the input control may provide enough inertia to cause the input control to continue motion after the user releases the input control. The safety limit for the commanded motion (and with reference to process 630 in FIG. 6), may be different depending upon whether the commanded motion is an insertion command, a retraction command, or some other command. For example, during an insertion command, when contact is not detected with the input control (e.g., track wheel), the control system may halt the commanded motion immediately upon loss of contact. In contrast, during a retraction command, when contact is not detected with the input control (e.g., track wheel), the commanded motion can continue.

In some embodiments, when the lock mode is entered, one or more alerts may be provided to the operator. In some examples, the one or more alerts may include sending a status message to a display screen, such as screen 420. In some examples, the one or more alerts may include changing a color and/or a shape on the display screen and/or flashing one or more items displayed on the display screen. In some examples, the one or more alerts may include activating an alert tone, outputting a spoken message, and/or the like. In some examples, the one or more alerts may include providing physical feedback, such as vibrating the input control console.

Once in the lock mode at process 650, method 600 may return to process 610 to determine whether affirmative contact by the operator with the one or more input controls has been reestablished and further commanded motion should be allowed.

One or more elements in embodiments of the invention (e.g., the processing of signals received from the input controls and/or control of the elongate device) may be implemented in software to execute on a processor of a computer system, such as control system 112. When implemented in software, the elements of the embodiments of the invention are essentially the code segments to perform the necessary tasks. The program or code segments can be stored in a non-transitory machine-readable storage media, including any media that can store information including an optical medium, semiconductor medium, and magnetic medium. Machine-readable storage media examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. As described herein, operations of accessing, detecting, initiating, registered, displaying, receiving, generating, determining, moving data points, segmenting, matching, etc. may be performed at least in part by the control system 112 or the processors thereof.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A control system for a device, the control system comprising:

a memory; and a processor coupled to the memory, the processor configured to:

receive, via one or more sensors, a contact signal indicating that an operator is in contact with a first input control of an input control console coupled to the control system;

determine whether the contact signal indicating that the operator is in contact with the first input control is an activation signal;

receive a contact signal indicating that the operator is in contact with a second input control of the input control console;

receive an input representing a commanded motion of the device at the first input control; and execute the commanded motion if the processor determines that:

the contact signal indicating that the operator is in contact with the first input control is the activation signal; and the operator is in contact with the second input control.

2. The control system of claim 1, wherein the contact signal indicating that the operator is in contact with the first input control is the activation signal if the contact signal indicating that the operator is in contact with the first input control indicates that more than one operator contact was received by the first input control.

3. The control system of claim 1, wherein the contact signal indicating that the operator is in contact with the first input control is the activation signal if the contact signal indicating that the operator is in contact with the first input control indicates that the operator is in contact with the first input control for a threshold time period.

4. The control system of claim 1, wherein the contact signal indicating that the operator is in contact with the first input control is the activation signal if the contact signal indicating that the operator is in contact with the first input control indicates that the operator is in contact with the first input control for a minimum contact period without motion of the first input control above a motion threshold.

5. The control system of claim 1, wherein the activation signal comprises a predetermined motion pattern for the first input control.

6. The control system of claim 1, wherein the processor is further configured to apply a safety limit to the commanded motion.

7. The control system of claim 6, wherein the safety limit comprises a maximum velocity.

8. The control system of claim 1, wherein the one or more sensors include one or more capacitive touch sensors, one or more pressure sensors, one or more proximity sensors to detect proximity of the operator to the input control console, one or more ultrasonic sensors, one or more vision sensors, one or more light walls, or one or more accelerometers of the input control console.

9. The control system of claim 1, wherein the processor is further configured to:

determine whether the operator is simultaneously in contact with the first input control and the second input control; and execute the commanded motion if the processor further determines that the operator is simultaneously in contact with the first input control and the second input control.

10. The control system of claim 9, wherein the processor is configured to determine that the operator is simultaneously in contact with the first input control and the second input control based on simultaneous receipt of the contact signal indicating that the operator is in contact with the first input control and the contact signal indicating that the operator is in contact with a second input control.

11. The control system of claim 9, wherein determining whether the operator is simultaneously in contact with the first input control and the second input control comprises:

determining whether the contact signal indicating that the operator is in contact with the first input control is received for a duration longer than a threshold duration; and determining whether the contact signal indicating that the operator is in contact with a second input control is received for a duration longer than a threshold duration.

12. The control system of claim 1, wherein the commanded motion is insertion motion of the device, and wherein contact with only one of the first input control or the second input control is needed for executing retraction motion or steering motion of the device.

13. A control system for a device, the control system comprising:

a memory; and a processor coupled to the memory, the processor configured to:

receive, via one or more sensors, a contact signal indicating that an operator is in contact with an input control of an input control console coupled to the control system;

determine whether the contact signal is an activation signal;

receive an input representing a commanded motion of the device at the input control;

execute the commanded motion if the processor determines that the contact signal is the activation signal; and apply a safety limit to the commanded motion, wherein the safety limit comprises ramping up a scale factor between movement of the input control and the commanded motion.

14. The control system of claim 13, wherein the contact signal is the activation signal if the contact signal indicates that the operator is in contact with the input control for a threshold time period.

15. The control system of claim 13, wherein the contact signal is the activation signal if the contact signal indicates that:

more than one operator contact was received by the input control; or the operator is in contact with the input control for a minimum contact period without motion of the input control above a motion threshold.

16. A method of operating a device, the method comprising:

receiving, by a control unit using one or more sensors, a contact signal indicating that an operator is in contact with a first input control of an input control console;

determining, by the control unit, whether the contact signal indicating that the operator is in contact with the first input control is an activation signal;

receiving, by the control unit, a contact signal indicating that the operator is in contact with a second input control of the input control console;

receiving an input representing a commanded motion of the device at the first input control; and executing the commanded motion based on a determination that:

the contact signal indicating that the operator is in contact with the first input control is the activation signal; and the operator is in contact with the second input control.

17. The method of claim 16, wherein the contact signal indicating that the operator is in contact with the first input control is the activation signal if the contact signal indicating that the operator is in contact with the first input control indicates that more than one operator contact was received by the first input control.

18. The method of claim 16, wherein the contact signal indicating that the operator is in contact with the first input control is the activation signal if the contact signal indicating that the operator is in contact with the first input control indicates that the operator is in contact with the first input control for a threshold time period.

19. A non-transitory machine-readable medium comprising a plurality of machine-readable instructions which when executed by one or more processors associated with a device are adapted to cause the one or more processors to:

receive, via one or more sensors, a contact signal indicating that an operator is in contact with a first input control of an input control console;

determine whether the contact signal indicating that the operator is in contact with the first input control is an activation signal;

receive a contact signal indicating that the operator is in contact with a second input control of the input control console;

receive an input representing a commanded motion of the device at the first input control; and execute the commanded motion if the one or more processors determine that:

the contact signal indicating that the operator is in contact with the first input control is the activation signal; and the operator is in contact with the second input control.

20. The non-transitory machine-readable medium of claim 19, wherein the contact signal indicating that the operator is in contact with the first input control is the activation signal if the contact signal indicating that the operator is in contact with the first input control indicates that more than one operator contact was received by the first input control.

21. The non-transitory machine-readable medium of claim 19, in the contact signal indicating that the operator is in contact with the first input control is the activation signal if the contact signal indicating that the operator is in contact with the first input control indicates that the operator is in contact with the first input control for a threshold time period.

* * * * *